(12) United States Patent
Kappeler et al.

(10) Patent No.: US 12,109,401 B2
(45) Date of Patent: Oct. 8, 2024

(54) STATE ESTIMATION FOR DRUG DELIVERY SYSTEMS

(71) Applicant: Ypsomed AG, Burgdorf (CH)

(72) Inventors: Krista Kappeler, Bern (CH); Leos Urbanek, Bern (CH)

(73) Assignee: Ypsomed AG, Burgdorf (CH)

( * ) Notice: Subject to any disclaimer, the term of this patent is extended or adjusted under 35 U.S.C. 154(b) by 1049 days.

(21) Appl. No.: 17/033,215

(22) Filed: Sep. 25, 2020

(65) Prior Publication Data

US 2021/0008288 A1 Jan. 14, 2021

Related U.S. Application Data

(63) Continuation of application No. PCT/IB2019/052470, filed on Mar. 27, 2019.

(30) Foreign Application Priority Data

Mar. 29, 2018 (EP) ..................................... 18164896

(51) Int. Cl.
*A61M 5/315* (2006.01)
*A61M 5/20* (2006.01)

(52) U.S. Cl.
CPC ........ *A61M 5/3157* (2013.01); *A61M 5/2033* (2013.01); *A61M 2205/3317* (2013.01);
(Continued)

(58) Field of Classification Search
None
See application file for complete search history.

(56) References Cited

U.S. PATENT DOCUMENTS 3,701,345 A * 10/1972 Heilman ................ A61B 6/481
600/432
4,914,566 A * 4/1990 Steutermann ........ G05B 19/291
251/129.05

(Continued)

FOREIGN PATENT DOCUMENTS

CN 101120618 A 2/2008
EP 3545991 A1 10/2019

(Continued)

OTHER PUBLICATIONS

International Search Report and Written Opinion received for International Application No. PCT/IB2019/052470 mailed on Jun. 13, 2019, 13 pages.

(Continued)

*Primary Examiner* — Manuel A Mendez
(74) *Attorney, Agent, or Firm* — Dorsey & Whitney LLP

(57) ABSTRACT

A flexible and reliable delivery state estimator or evaluator is provided for a drug delivery device. The proposed delivery status estimation architecture includes a position sensor that provides a continuous position sensor signal indicative of a current position of a component of the delivery device movable continuously from a first to a second component position, as well as a position discriminator that redefines the continuous position sensor signal to generate an approximate binary input signal on behalf of a state estimator. The discriminator absorbs any difficulty that may arise from a limited reproducibility or enhanced variability of the original continuous sensor signal, specifically including a user-originated signal spread in a movement of a needle protection sleeve of the delivery device.

18 Claims, 4 Drawing Sheets

(52) U.S. Cl.
CPC . *A61M 2205/3584* (2013.01); *A61M 2205/52* (2013.01); *A61M 2205/581* (2013.01); *A61M 2205/582* (2013.01); *A61M 2205/583* (2013.01); *A61M 2205/587* (2013.01)

(56) References Cited

U.S. PATENT DOCUMENTS

| | | | |
|---|---|---|---|
| 5,034,004 | A * | 7/1991 | Crankshaw ......... A61M 5/1456 D24/111 |
| 6,658,577 | B2 | 12/2003 | Huppi et al. |
| 6,743,202 | B2 * | 6/2004 | Hirschman ....... A61M 5/14546 604/151 |
| 9,492,620 | B2 * | 11/2016 | Schabbach .......... A61M 5/3146 |
| 9,774,749 | B1 | 9/2017 | Skrainar et al. |
| 10,967,133 | B2 | 4/2021 | Pedersen et al. |
| 2002/0178388 | A1 | 11/2002 | Huppi et al. |
| 2007/0046255 | A1 | 3/2007 | Kim |
| 2008/0278221 | A1 | 11/2008 | Rowland |
| 2010/0069830 | A1 | 3/2010 | Grigorov |
| 2011/0270188 | A1 | 11/2011 | Caffey et al. |
| 2012/0089114 | A1 | 4/2012 | Hemond et al. |
| 2016/0047685 | A1 | 2/2016 | Blei et al. |
| 2017/0368256 | A1 | 12/2017 | Nessel et al. |
| 2018/0043105 | A1 | 2/2018 | Nazzaro et al. |
| 2018/0064881 | A1 | 3/2018 | Whalley et al. |
| 2021/0008294 | A1 | 1/2021 | Gentz |

FOREIGN PATENT DOCUMENTS

| | | |
|---|---|---|
| EP | 3545992 A1 | 10/2019 |
| EP | 3545993 A1 | 10/2019 |
| WO | 2004023637 A1 | 3/2004 |
| WO | 2008049609 A1 | 5/2008 |
| WO | 2011022850 A2 | 3/2011 |
| WO | 2016118736 A1 | 7/2016 |
| WO | 2016142727 A1 | 9/2016 |
| WO | 2017148857 A1 | 9/2017 |
| WO | 2018036938 A1 | 3/2018 |
| WO | 2018041798 A1 | 3/2018 |
| WO | 2018064784 A1 | 4/2018 |
| WO | 2019186381 A1 | 10/2019 |
| WO | 2019186412 A1 | 10/2019 |
| WO | 2019186413 A1 | 10/2019 |

OTHER PUBLICATIONS

Extended European Search Report issued in European Patent Application No. 18164896.5, mailed on Jul. 2, 2018, 8 pages.
International Preliminary Report on Patentability received for International Application No. PCT/IB2019/052427, mailed on Sep. 29, 2020, 6 pages.
International Preliminary Report on Patentability received for International Application No. PCT/IB2019/052470 mailed on Sep. 29, 2020, 9 pages.
International Preliminary Report on Patentability received for International Application No. PCT/IB2019/052471, mailed on Sep. 29, 2020, 9 pages.
English Translation of Chinese publication No. 101120618 A, provided by the European Patent Office with the issuance of the Extended European Search Report.
International Search Report and Written Opinion received for International Application No. PCT/IB2019/052471, mailed on Jun. 13, 2019, 14 pages.
International Search Report and Written Opinion received for International Application No. PCT/IB2019/052427, mailed on Jun. 17, 2019, 10 pages.
Extended European Search Report received for European Application No. 18164906.2, mailed on Oct. 10, 2018, 6 pages.
Extended European Search Report received for European Application No. 18164883.3, mailed on Nov. 15, 2018, 8 pages.

* cited by examiner

CH0

TFT
y
BST
x

STATE ESTIMATION FOR DRUG DELIVERY SYSTEMS

CROSS-REFERENCE TO RELATED APPLICATIONS

This application is a continuation of Patent Application No. PCT/IB2019/052470, filed Mar. 27, 2019, entitled "STATE ESTIMATION FOR DRUG DELIVERY SYSTEMS," which in turn claims priority to European Patent Application No. 18164896.5, filed Mar. 29, 2018, entitled "STATE ESTIMATION FOR DRUG DELIVERY SYSTEMS", each of which is incorporated by reference herein, in the entirety and for all purposes.

FIELD OF THE INVENTION

The present invention relates to drug delivery systems for delivering, administering, injecting, infusing or dispensing liquids comprising a drug, medicament, or active ingredient. One variant of the invention begins from a method of determining a delivery status of a drug delivery device and from an electronic module attachable to a disposable injection device.

BACKGROUND OF THE INVENTION

A variety of diseases exist that require regular treatment by subcutaneous administration of a medicament, and a number of drug delivery devices have been developed to support a patient in accurately and controllably delivering an amount of drug in a self-administration process. Delivery devices include injection devices that are removed from the injection site after each medication event or drug delivery process, as well as infusion devices with a cannula or needle that remains in the skin of the patient for a prolonged period of time. Disposable delivery devices are adapted to deliver a drug from a container such as a pre-filled syringe that is not intended to be replaced or refilled by the patient. Reusable, semi-reusable, or hybrid delivery devices have at least a container and possibly also a container holder that may be replaced by the patient, or a cartridge that may be refilled, while some components of the device may be reused with the replaced or refilled drug container. By way of example, diabetes may be treated by administration of insulin by the patients themselves with the help of multi-variable-dose insulin injection pens or infusion pumps.

Fixed dose disposable injection devices include single-dose injection devices such as auto injectors or patch injectors as well as multi-dose injection devices such as fixed dose injectors. Auto-injectors automatically deliver a fixed dose of liquid drug from a pre-filled syringe by-means of a pre-loaded injection spring powering a piston rod and shifting a piston in a syringe barrel. Patch injectors or ready-to-use pre-filled wearable bolus injectors are applied or adhered to the skin of the patient in view of a single dose injection taking between thirty-seconds and several minutes. Fixed-dose injectors have a single, non-variable dosage volume, or may provide a limited number of fixed, non-variable injection dosage volumes for the user to choose from.

Disposable delivery devices may be complemented by a monitoring or control unit being part of a reusable electronic module or auxiliary device adapted to be attached successively to the device housings of plural disposable delivery devices. The monitoring unit serves to monitor the delivery process, in order to proactively prevent or retroactively recognize incorrect handling of the device and to keep track of the doses already applied. In addition to generating data related to an instantaneous status, condition, or use of the delivery device, information on the drug type, cartridge batch, and/or expiration date may be evaluated by the monitoring unit. To that end, the electronic module comprises a delivery status sensing unit for tracking a progress of a medication event performed by means of the delivery device and/or for reading drug information that is stored on a machine-readable tag mounted to the device housing. The module may further comprise a status indicator for signaling status and drug information to a user, and a wireless communication unit for communicating status and drug information to a nearby mobile device or medical gateway. All these units are supplied with power from an energy storing unit of the electronic module, wherein the electronic module generally excludes any kind of electrically powered mechanical actuator or motor load. An exemplary electronic module with a sensing unit capable of discerning various operational states of a disposable auto-injector is disclosed in PCT/CH2017/050004.

A monitoring or control unit with the aforementioned sensor, indicator and communication functionalities may be part of a reusable electronic delivery device and as such be integrated into a device housing of the delivery device comprising the reusable components. In this case, the electronic delivery device may be a reusable injection pen with a monitoring unit and a manually powered delivery drive requiring a user to manually provide the energy to move the piston or to load a drive spring. The electronic delivery device may also be a reusable infusion pump with a monitoring unit and with a motor driving the piston automatically. All sensing, reading, evaluating, indicating, data processing, and communicating facilities of the monitoring unit are powered from an energy storing unit of the reusable delivery device.

Delivery status sensing means generally detect a linear and/or rotational movement of a movable component of the delivery device that occurs during a medication event. From the detected ongoing or completed displacement of the component, a delivery status is inferred and communicated to a user. The definition of a delivery status in this context may be independent of certain aspects of component movement, such as for instance a rotation direction of a screw-type plunger rod, or an absolute sensor signal amplitude. Accordingly, distinct types of delivery devices may well be characterized by the same formal delivery states, irrespective of the fact that certain inter-type variations in design geometry or in properties of the materials chosen may influence an unprocessed sensor signal.

Within one delivery device type, and even within successive delivery events performed by means of one single device, characteristics of component motion such as a speed of the moving component may vary to a large extent. This may be due to a viscosity of or to a residual volume of the liquid to be expelled, or depend on the type of tissue into which the liquid is injected. In delivery devices with user driven or guided component movement, such movement may be strongly dependent on a force or pressure that the user is able or willing to provide. Accordingly, a speed of the component may vary significantly, and give rise to a corresponding variance or spread in the unprocessed sensor signal that represents the component movement. Such variations may be more pronounced for user-driven movements against the bias of a return spring than for trigger movements that include a high initial resistance to be overcome by the user. Inserting a cover sleeve or needle protective sleeve into the body of an auto-injector upon contact with the injection site may be a prominent example of a user-dependent component movement with enhanced variability that ideally is accounted for in a delivery status determination.

In the present context, the terms "substance", "drug", "medicament" and "medication" are to be understood to include any flowable medical formulation suitable for controlled administration through a means such as, for example, a cannula or a hollow needle, and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

DESCRIPTION OF THE INVENTION

It is an objective of the invention to enable a flexible and reliable delivery state estimation or evaluation for a drug delivery device. This objective is achieved by a method of determining a delivery status and by a monitoring unit for a delivery device according to the present disclosure. Various embodiments are evident from the accompanying patent claims.

According to the invention, a delivery status of a drug delivery device with a container holding a liquid drug to be expelled in a drug delivery event is estimated or evaluated by the following means and steps.

A position sensor for detecting and providing a continuous position sensor signal indicative of, in particular proportional to, an instantaneous or current position of a component of the delivery device movable from a first, or initial, to a second, or later, component position.

A position discriminator for generating, from the continuous component position signal, a binary position signal, or binary position information, with the two values of the binary signal or information being associated with the first and the second component position, respectively. The binary position signal is indicative of, or re-defining, whether the component may be considered to be in, or to be assigned to, the first or the second component position.

A status evaluator or state estimator for deriving the delivery status from the binary position signal.

The sensing, discriminating, and evaluating means may be part of a monitoring unit of a reusable drug delivery device, or of an electronic module for removable attachment to a device housing of a disposable drug delivery device. The monitoring unit may optionally include a status indicator for indicating the delivery status, communication means, and a power supply for supplying power to the sensing, discriminating, evaluating, indicating and/or communicating means.

The proposed delivery status determination architecture or concept includes a position discriminator that augments or redefines an original continuous sensor signal to generate an approximate, augmented binary input signal on behalf of a state estimator or evaluator. The continuous position sensor signal represents a continuous, uninterrupted, slow or fast movement of the component of the delivery device from the first to the second component position. The component movement may be arbitrarily small and require a transducer, such as a force or pressure sensor, to generate the continuous sensor signal. The discriminator block or logic component handles or absorbs any difficulty that may arise from a limited reproducibility or enhanced variability of the original continuous sensor signal, specifically including a user-originated signal spread. The state estimator block or logic component may therefore operate on idealized, updated binary data and possibly be restricted to a state evaluation based on a table coding the delivery states. Such a table may assign each status to a combination of plural discrete component position signals originating from plural moving components, wherein such assignment may additionally depend on a preceding delivery state or other history information. Accordingly, a state estimator or evaluator operating on well-defined discrete position signals facilitates portability or re-usability across different delivery device types, and provides flexibility for status evaluation extension. The latter may be appropriate if additional position signals are considered and/or additional states based on existing position signals are being introduced at a later time or for a different delivery device.

The state estimation process may be executed in real time, and the status may be updated in discrete time steps as soon as a new sample of the position signal is provided, without any requirement to wait for the delivery event to complete. Nevertheless, the original continuous position signal or the processed binary position signal may be recorded and stored for post-delivery analysis. Storing the processed binary signals for later or batch status evaluation, or for transmission via the communication facility, demands less storage space than the original continuous sensor signal. The position discriminator block and the status estimator block (or a logic component, such as a computer program, comprising either) may be loaded to, and executed by, one and the same processing unit of a monitoring unit, such as a Field Programmable Gate Array FPGA, an Application-Specific Integrated Circuit ASIC, or a microcontroller, or by distinct processing units including correspondingly configured or programmed circuitry. A computer program product including computer readable code, specifically for later adaptations or modifications of the state evaluation block, may be stored off-system and loaded to the monitoring unit as an update after assembly thereof.

The proposed discriminator block may include a straightforward impulse detection which relies on the difference between a running average and the current value of the continuous position signal. The running average of the signal is the median, mean, or any other characteristic value of a moving window comprising the latest signal samples. Taking the difference between the current signal and the average reveals a peak for every step in the original signal, which is recognized by using a threshold method. Impulse detection only needs few computational steps and introduces no delay. On the other hand, when the original signal changes slowly the difference between the running average and the current signal will be suppressed. Increasing the window size of the median filter may help but lead to unacceptably long delays to establish component movement. An alternative discriminator based on a derivative of the continuous position signal runs the risk of falsely identifying small excursions of the signal, which may for instance be induced by a shaking hand of a user, as valid component movements.

In a one variant of the invention, the position discriminator block or logic detects changes in the original continuous signal by subtracting a current signal from a slow tracker signal, including the specific steps of:

updating, for a continuous component position signal with a first or initial value and a second or later value below the first value, a top, or maximum, slow tracker signal, and/or updating, for a continuous component position signal with a first or initial value and a second or later value above the first value, a bottom, or minimum, slow tracker signal, determining a difference between a current or instantaneous value of the continuous component position signal and either one of the updated top or bottom slow tracker signal, comparing the difference to a pre-determined threshold to identify the binary signal value assignable to the current value of the continuous position signal.

For each time step t, upon provision of the current or most recent signal value sample at time t, the update of the top and bottom slow tracker signals involves calculating, from a previous value at a previous time step t' and based on a relaxation parameter, a relaxed or provisional tracker signal value at time t. The relaxed tracker signal value is replaced by the current value if the latter exceeds the relaxed top tracker value, or is below the relaxed bottom tracker value, such as to form a top or bottom envelope signal. In these cases, the updated difference is obviously equal to zero. If the relaxed tracker signal does not overshoot or undershoot, respectively, the updated slow tracker value is set to the relaxed tracker signal value. Updating a slow tracker signal requires only limited computational resources, and allows to reliably detect even the smallest position signal variations.

The relaxed tracker signal represents a drift or decay of the slow tracker signal based on the relaxation parameter, which includes a linear drift rate or an exponential decay time indicative of, or capturing, an estimated deviation of the position sensor signal independent of actual component movements. The full benefit of the tracker signal is apparent when noise is present in the continuous position signal and noise-induced signal excursions of a length comparable to the duration of a movement of the device component are observed. The relaxation is taking place in a direction from the first towards the second value of the continuous component position signal, and may coincide with a sensor-inherent or environmentally-induced signal drift. Typical relaxation parameters represent a signal deviation of the order of a few percent within a nominal duration of a delivery event, or a deviation of the order of the initial signal within a period exceeding the nominal duration of a delivery event by a factor of 10 to 100.

The initial and final value of the continuous position signal need to be known at least approximately for the pre-determination of the threshold. The threshold may be chosen anywhere in between these values, and preferably is closer to the final value than to the initial value, and may be open for adaptation during operation. The proposed relaxation of the tracker signal may equivalently be replaced by an adaptive correction of the current signal in order to account for a drift. Likewise, calculating an instantaneous difference for comparison to a relative threshold related to a maximum difference is presumed equivalent to comparing the current signal value to an absolute threshold depending on, or varying with, the slow tracker signal.

In one embodiment of the invention the relaxation of the slow tracker signals is described by a constant drift parameter implying a linearly, including stepwise, varying slow tracker signal. For a continuous component position signal with a first or initial value and a second or later value below/above the first value, the top/bottom provisional tracker signal value at time t is lower/higher than the previous slow tracker signal value at time t' by a pre-determined slow tracker step height. In other words the linearly varying slow tracker signal is, during relaxation, a step function with a predefined step height and a finite step width given by the sampling or update rate. Preferably, the fast tracker signals may likewise include a fast tracker step height that limits the tracking ability of the fast tracker and introduces a temporary delay between the continuous position signal and the fast tracker. The fast tracker step height is, at equal step width, distinctly larger than the slow tracker step height. In addition or alternatively, step width may be distinct, and considerably shorter for the fast tracker.

In an one variant, the position discriminator defines, for a continuous component position signal with a first or initial value and a second or later value below/above the first value, a top/bottom slow tracker signal as a baseline. In addition the position discriminator defines, for the continuous component position signal with the second value below the first value, a fast bottom tracker signal slightly smaller than and swiftly approximating the continuous position signal, without exceeding the latter. The difference to be compared to a threshold is taken between the top slow tracker signal and the fast bottom tracker signal of the continuous component position signal. The position discriminator defines, for the continuous component position signal with the second value above the first value, a fast top tracker signal slightly larger than and swiftly approximating the continuous position signal without falling below the latter. The difference to be compared to a threshold is taken between the fast top tracker signal and the bottom slow tracker signal of the continuous component position signal.

In an embodiment of the invention, the device component, after resting immovable in the second component position for a minimum dwell time or interval during which another component of the delivery device moves in turn, may continue to a third position or back to the first position. In the case of a third or further component position, the binary signal may be part of a discrete signal with more than two well-distinct values representing the sequentially reached positions of the moving component. A second or further threshold is pre-determined to derive the discrete component position signal, with the slow tracker signal or baseline evolving as described. In other words, the two distinct thresholds define a bandwidth associated with the intermediate discrete component position. Furthermore, in analogy to the second position, two distinct thresholds may even define a transitional discrete signal value for a monotonically evolving component, without there actually being a pause or plateau at an intermediate component position.

Another variant of the monitoring unit includes a position discriminator for generating a further binary position signal from a further continuous position sensor signal provided by a further position sensor and indicative of, or varying proportional to, an instantaneous position of a further component of the delivery device. The further component is movable from a further first or initial position to a further second or later position, with which positions the two values of the binary position signal are being associated. The status evaluator is configured to derive the delivery status from both of the binary position signal and the further binary position signal.

In one embodiment of the monitoring unit, the position sensor is adapted or designed to measure a position signal of a device component being moved manually by or through a user of the delivery device. The position signal changes at a rate that is dependent on the user handling speed, and the component movement includes pushing/releasing a button, inserting a cover sleeve against a restoring force of a cover sleeve spring, turning a dose dialing button.

In another embodiment, the auto-injector comprises a cover sleeve or needle protective sleeve for protecting a needle of the syringe after removal of the auto-injector from the injection site. Incidentally the cover sleeve may also protect a needle extending distally of a device housing before use, and/or serve as a trigger detecting contact with the skin of the user. Upon removal of the auto-injector from the injection site the needle protective sleeve is biased to a needle protecting position by a cover sleeve spring, and locked in this position by a locking means. The movement of the cover sleeve itself or of a base of the cover sleeve spring moving concurrent or in parallel with the cover sleeve is observed by the position sensor. Furthermore, start and end of a substance ejection as well as injection device lift-off may be detected by the injection status sensing means and advantageously combined to obtain a characterization of the ongoing injection process or medication event, in order to track whether an injection event has occurred according to the medication schedule but also whether that injection was successfully completed or not.

In one prominent or common use case the manually movable component is displaced in the interior, and with respect to a housing, of the delivery device. Nevertheless, in another embodiment, the position sensor is adapted to provide a continuous position sensor signal indicative of a distance of the delivery device from a target injection site. In other words, the movable component may include any component of the delivery device, and the position sensor may provide an estimate of distance between, for instance, a skin-contact electrode of a patch injector as the exemplary delivery device, and the skin of the user.

In a further embodiment, the sensing, discriminating, and evaluating means of the monitoring unit are comprised in an electronic module for removable attachment to a device housing of a disposable drug delivery device. The electronic module further comprises a tag reader for reading, once the electronic module is being or has been attached to a delivery device, information from a machine-readable tag mounted to a device housing of the drug delivery device. The information comprises parameter values relevant for the generation of the binary position signal by the position discriminator, such as the discriminator thresholds and relaxation parameters introduced above.

In the present context, the term "injection device" refers to a generally pen-shaped device with an elongate device body defining a longitudinal main device axis. The term "distal end" refers to the end of the injection device where an injection needle is located, the term "proximal end" designates the opposite end thereof.

BRIEF DESCRIPTION OF THE DRAWINGS

The subject matter of the invention will be explained in more detail in the following text with reference to preferred exemplars, embodiments which are illustrated in the attached drawings, in which.

The reference symbols used in the drawings, and their primary meanings, are listed in summary form in the list of designations below. In principle, identical parts are provided with the same reference symbols in the figures.

DETAILED DESCRIPTION OF PREFERRED EMBODIMENTS

Figure 1:
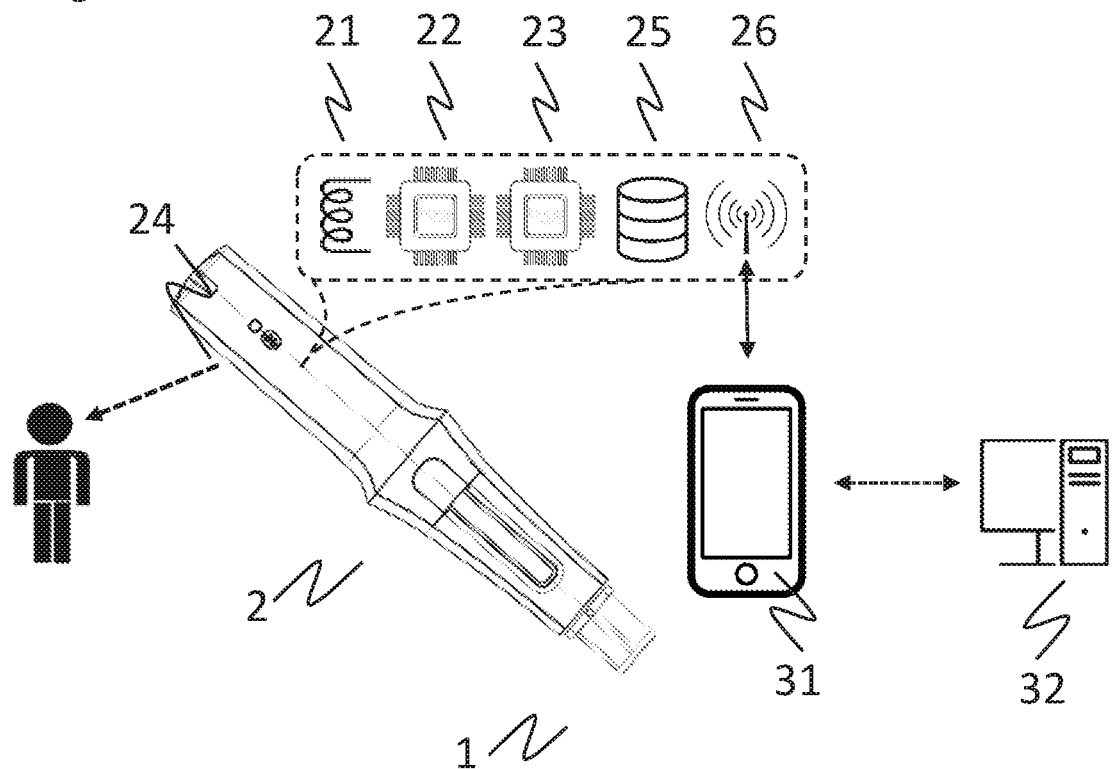
FIG. 1 depicts a variant of a medical monitoring system with an auto-injector.

FIG. 1 depicts an embodiment of a medical monitoring system comprising an auto-injector as an exemplary disposable delivery device 1, an electronic module 2 releasably attached to a device housing of the injection device, and a mobile device 31 such as a smartphone or tablet device running a dedicated application program; or a laptop computer configured accordingly. The mobile device 31 is communicatively connected via a data communication network, e.g. the Internet, to a remote server, cloud based computing facility, or expert system 32. The electronic module 2 includes a monitoring unit with a position sensor 21, a position discriminator 22, and a status evaluator 23. The electronic module further comprises a status indicator 24 such as a LED, buzzer, vibration alarm, or any other type of human-machine interface (HMI) element for providing visual, acoustic, or tactile feedback about a derived injection status. A memory or data storage unit 25 (with associated unit) is adapted to store status or delivery information. The electronic module also comprises a communication unit 26 for wireless transmission of an injection status or drug status to the mobile device 31 via Bluetooth Low Energy (BTLE) or equivalent short or near range wireless communication technology. The electronic module 2 has a rear, or proximal, part where some or all electronic components as described are located.

Figure 2:
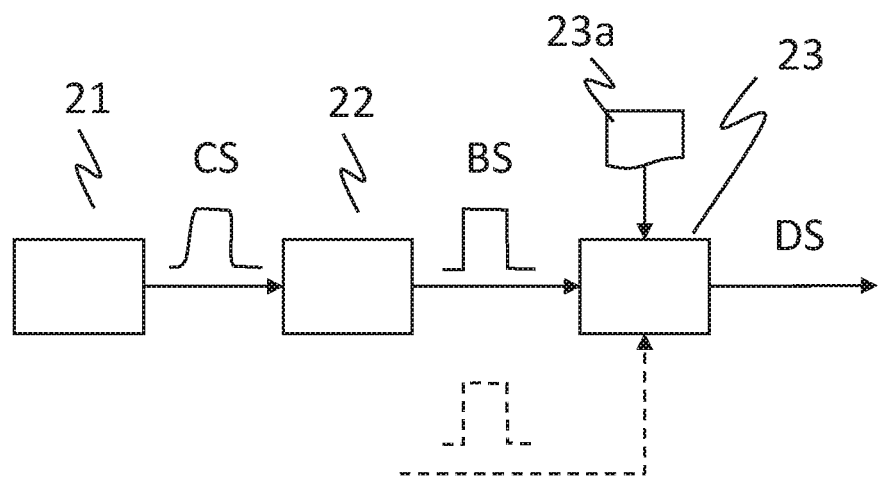
FIG. 2 depicts a flow chart with selected blocks of the monitoring unit.

FIG. 2 depicts a flow chart of the pertinent blocks/logic components of the monitoring unit, of which the position sensor 21 provides a continuous position sensor signal CS to the position discriminator 22 that in turn generates a binary position signal BS based on the continuous position signal. The binary position signal is evaluated, together with optional further binary position signals (dotted lines), by the status evaluator 23, based on an evaluation table 23a coding the delivery states as a combination of binary position signal values, to identify a delivery state DS.

At least the position sensor 21 of a monitoring unit with block-wise state estimation may be part of, or embedded in, a delivery device that is designed or adaptable to accommodate sensing elements. In this embodiment, contact-based sensing means relying on position dependent electrical resistance or mechanical force may be employed, such as a piezo-based force or pressure transducer provided adjacent to the base of a linear compression spring. Alternatively, the monitoring unit may be part of an electronic module 2 adapted to be removably attached to a device housing of an delivery/injection device 1 as depicted in FIG. 1. In this case, contact-free, non-invasive sensing means are preferably employed, based on electrical, optical, acoustical signals indicative of an injection process executed by means of the injection device 1 and well-discernable outside of, but reasonably close to, the device. Specifically, the injection status sensing means may include an electrical sensor such as a contact-free inductive or capacitive sensor to detect initial, intermediate, and final values of, and/or corresponding changes or differences in, a static or alternating electromagnetic field or flux depending on a position or displacement of a magnetic or inductively responding device component. The inductive position sensor includes an inductive sensor comprising a sensor induction coil and a sensor control unit for detecting, in an attached state of the electronic module 2 and the injection device, an inductance of the sensor induction coil which is dependent on a position of a component of the injection device that is at least partly made of a magnetic or of an electrically conductive material. The electronic module may also operate with non-invasive sensing means that depend on a sound mechanical contact with the delivery device, such as inertia, vibration, force or pressure measurements.

The exemplary disposable injection device 1 in FIG. 1 is an auto-injector for automatically injecting a liquid medicament as described for instance in EP 2781230. The auto injector has an elongate casing including a syringe holder part for accommodating an active agent container or prefilled syringe with an injection needle at a distal end. A driving or injection spring is provided for powering a piston rod and shifting a piston comprised in the container in order to deliver the active agent. The auto-injector also includes a cover sleeve or needle protective sleeve that surrounds the needle in a first position, and that may be axially moved in a proximal direction towards a second position. When the distal end of the auto-injector is pressed onto the skin of a patient, the cover sleeve is displaced in a proximal direction, and a cover sleeve spring is loaded or tensioned. Towards the end of this initial cover sleeve retraction, a click element is displaced in a distal direction by means of the relaxing injection spring, which in turn causes an additional tensioning of the cover sleeve spring. Alternatively, the click element is displaced in a proximal direction by means of the relaxing cover sleeve spring. At the end of an ejection, an end-click element is released to move in a proximal direction under the effect of the injection spring or of the cover sleeve spring until it abuts and generates an end-click.

A conductive spring section including two winding turns that at least partially contact or overlap is preferred for being evaluated as a moving component in the context of the present invention. Such spring sections may be formed anywhere along a compressive spring, but are naturally found at a base, foot, or end of the spring. The base of the cover sleeve spring may comprise base winding loops with a diameter adapted to the diameter of the cover sleeve, and hence radially close to a circumferential device housing and at minimum radial distance to the sensor induction coil. Other conductive spring bases, such as those of a compressive injection spring or of a release button restoring spring, likewise appear suitable for an inductive position sensor. The spring base may include a first helical winding with an electrical contact between a first turn of the winding and a second, adjacent winding turn at a point of overlap, permitting the flow of circular currents. Such an electrical contact may be established preferably by laser, spot, or resistive welding or soldering techniques applied to the first and the second turn of the winding at a point of contact or overlap. Other techniques may also be suitable for preparing the contacting surfaces in order to enable a galvanic contact of low resistance and/or in order to mechanically stabilize the spring base and prevent the end turn from radial misalignment. In addition to the circular current, eddy currents circulating independently of a conductor topology in the bulk of the conductor may also contribute to the inductive response or feedback of the spring section.

Figure 3:
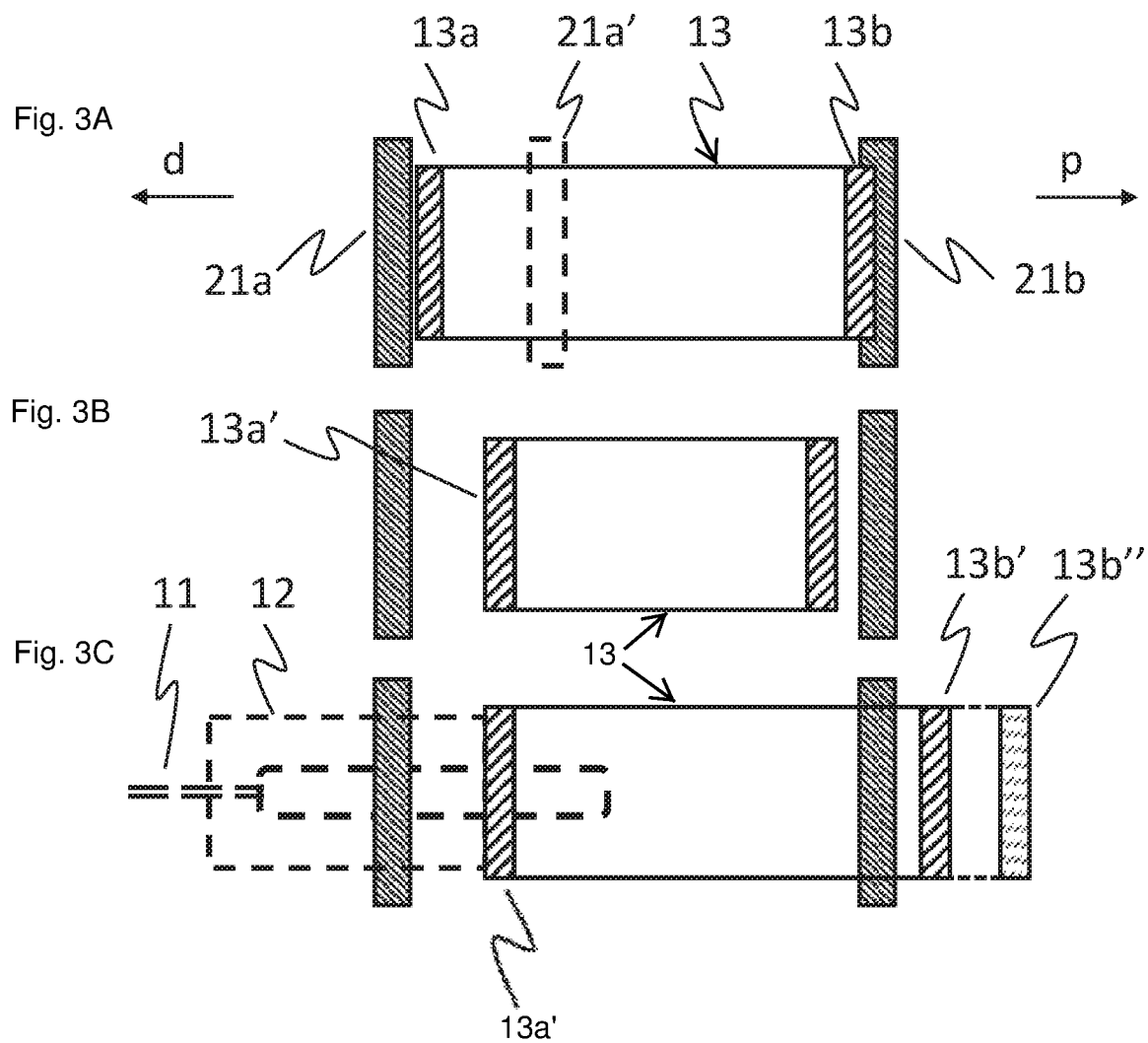
FIGS. 3A-3C depict a relative arrangement of sensor induction coils and spring bases in an initial state and two additional positional states of spring bases of a device cover sleeve.

FIG. 3A depicts schematically a relative arrangement of the sensor induction coils 21a, 21b and the cover sleeve spring bases 13a, 13b in an initial state of the cover sleeve spring 13. FIG. 3B depicts a compressed cover sleeve spring 13 with the first cover sleeve spring base 13a' having moved in proximal direction (p) by virtue of the retracted cover sleeve, and with the second cover sleeve spring base 13b having moved in distal direction (d). FIG. 3C depicts the cover sleeve spring 13 with the first cover sleeve spring base 13a' having moved proximally and with the second cover sleeve spring base now also having moved proximally, to position 13b', prior to drug ejection. Once the piston has reached its distal end position, the end-click element is released and accelerated in distal direction by one of the injection spring or the cover sleeve spring undergoing an ultimate expansion. In the latter case, the second cover sleeve spring base will move further proximally to position 13b". Incidentally, the FIG. 3C arrangement additionally depicts (in broken lines and schematically) a retracted cover sleeve 12 and the exposed needle or cannula 11 of a syringe or container held by the delivery device. The cover sleeve 12 is coupled to the cover sleeve spring to move conjointly between a first, initial and/or eventually final position in which the cover sleeve 12 essentially surrounds a needle of the injection device and a second, operational position in which the cover sleeve exposes the needle. On the other hand, the click sound generating elements that are arranged proximally of, and move jointly with, the proximal base 13b of the cover sleeve spring are not depicted.

In the proposed delivery status determination architecture including a state estimator block distinct from a position discriminator, only the latter needs to be modified when passing from the arrangement of FIG. 3B to the arrangement of FIG. 3C. Specifically, the second cover sleeve spring base 13b undergoing an initial movement in distal or proximal direction prior to drug ejection at most requires an additional change in sign when converting the continuous sensor signal into the binary signal, such that the state recognition block can be reused integrally.

Arranging the first, or front, sensor induction coil 21a at the distal side of the expanded, or first, position of the first cover sleeve spring base 13a has the advantage that the signal detected is rather independent of the actual cover sleeve displacement or stroke. Arranging the first sensor induction coil at an alternative position 21a' (indicated in broken lines in FIG. 3A) proximally of the compressed, or second, position 13a' of the first cover sleeve spring base (FIG. 3B) is likewise possible. With the above exemplary auto-injector and monitoring unit, an injection process is characterized by a sequence of four events that are observable with the two inductive sensor means of FIGS. 3A-C as the displacements of the first and the second spring base of the cover sleeve spring 13.

Figure 4:
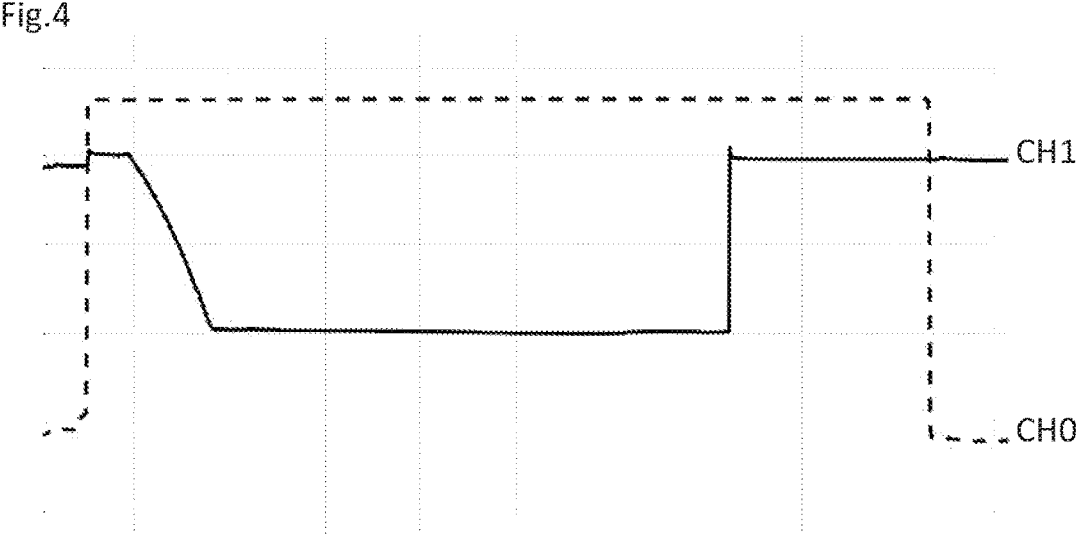
FIG. 4 shows two continuous position signals recorded during an injection event.

FIG. 4 depicts two exemplary continuous signals recorded during an injection performed with an auto-injector as described, in arbitrary units and over a time scale of a few seconds. The first signal (channel CH0, broken line) originates from a distal or front inductive sensor and represents the movement of the cover sleeve or, equivalently, of the distal base of the cover sleeve spring as the first device component. The second signal (channel CH1, continuous line) results from a proximal or rear inductive sensor and is indicative of a start and end of the ejection of medication and results from a proximal base of the cover sleeve spring. Both sensor signals may be pre-processed, including filtering by an average filter in order to remove noise without adding large delays, and converting into digital signals at an adaptable sampling rate between 1 and 1000 Hz, and preferably between 10 and 100 Hz.

Figure 5:
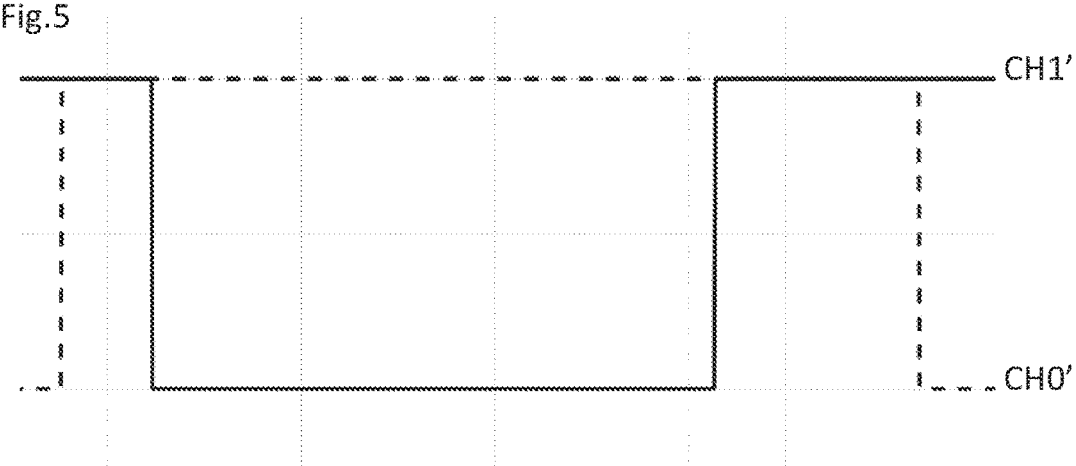
FIG. 5 shows corresponding binary position signals.

FIG. 5 depicts the binary output of the position discriminator when provided with the continuous position signals of FIG. 4. The pre-processed signal of CH0 is tracked or characterized by a slow bottom tracker signal and a fast top tracker signal. The pre-processed signal of CH1 is tracked by a slow top tracker and a fast bottom tracker. The slow trackers represent a baseline of the signal and the fast trackers approximate the instantaneous or current signal such that the latter is always in a band between the baseline and the fast tracker signal. The difference between top and bottom tracker is calculated for both channels as a measure of how much the current signal deviates from the baseline. Comparison of the calculated difference to a pre-determined, channel-specific and properly calibrated threshold allows to define the binary position signal. For instance, if and as long as for the first signal the difference exceeds the threshold, the binary signal CH0' is set to one or "on", otherwise to zero or "off". For the second signal, if and as long as the difference is below the applicable threshold, the binary signal CHF is set to one or "on". The assignment of the binary states may be inverted independently for any one or both of the two signals.

Figure 6:
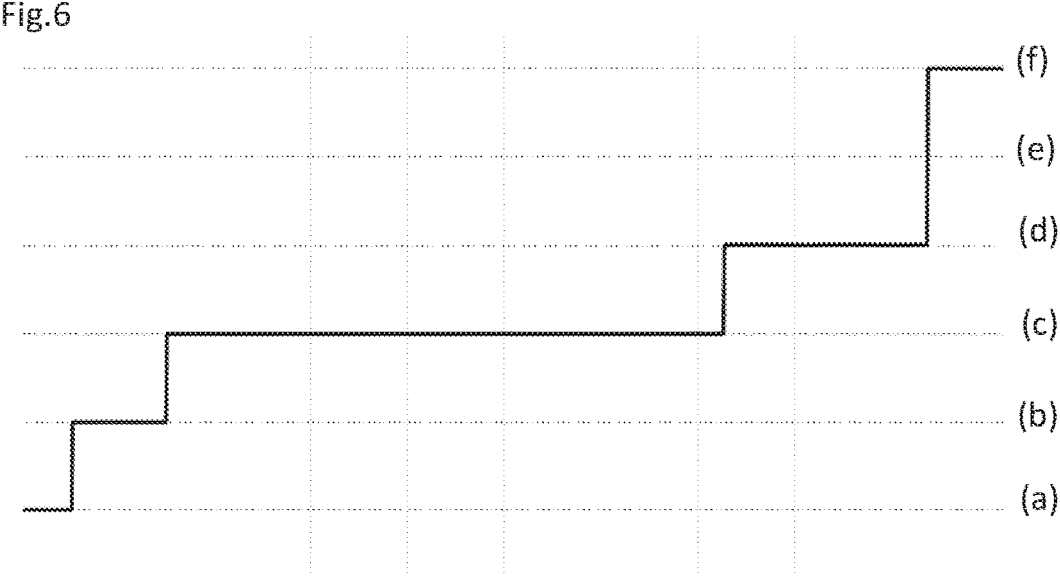
FIG. 6 shows the evaluated consolidated state evolution.

FIG. 6 depicts the evaluated consolidated state evolution as determined by the state evaluator or state machine based on the binary position signals of FIG. 5. The following states are being defined and complemented by suitable inter-state events.

(a): INITIAL: initial state
(b): TRANSITION: transitional state between INITIAL and EJECT MEDICATION.
(c): EJECT MEDICATION: eject medication into body
(d): HOLDING: holding the auto-injector at injection site
(e): AIR SHOT: eject medication into air
(f): FINAL: final state Each of the aforementioned states is assigned a horizontal broken line in FIG. 5 in the order given. In a regular injection event, the states (a), (b), (c), (d) and (f) are successively entered by the delivery system as indicated by the continuous stair-case line. The air shot state is defined by the binary position value zero in both the first signal CH0' and the second signal CH1', implying an incomplete ejection and an expanded cover sleeve (due to premature needle retraction). This abort state occurs when the user removes the auto-injector from the injection site prior to completion of the fluid ejection, and replaces the holding state. It is evident that the initial and the final state are assigned to a same combination of binary component positions (CH0' off, CH1' on) and distinguished by their history. The same applies to the transition and the holding state (CH0' on, CH1' on); again they are distinguished by their preceding state (transition only occurs following initial). Depending on the delivery device design, the transition state may be considerably shorter than depicted, and hence rather qualify as an inter-state event.

Figure 7:
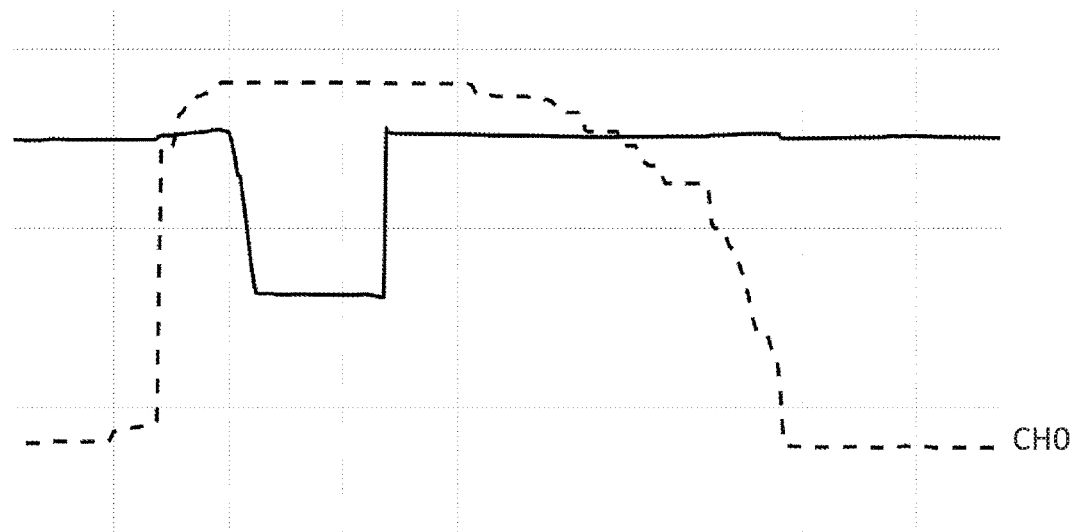
FIG. 7 shows two continuous position signals with slow device removal.

FIG. 7 depicts two exemplary continuous signals recorded during a different injection performed with the auto-injector. In this case, the needle has been removed from the injection site very slowly, causing a slow change in the first signal CH0 from the intermediate value back to the initial value. Similar ill-defined transitions in the first continuous position signal may occur because of a slow insertion of the needle. On the other hand, if the tissue into which the needle is inserted provides an increased resistance against fluid dispersion, the second signal may present a slower decrease. The proposed method has been proven to be capable of defining sharp and reasonable signal steps even for the soft, more gradual transitions and corresponding signal ramps as described.

Figure 8:
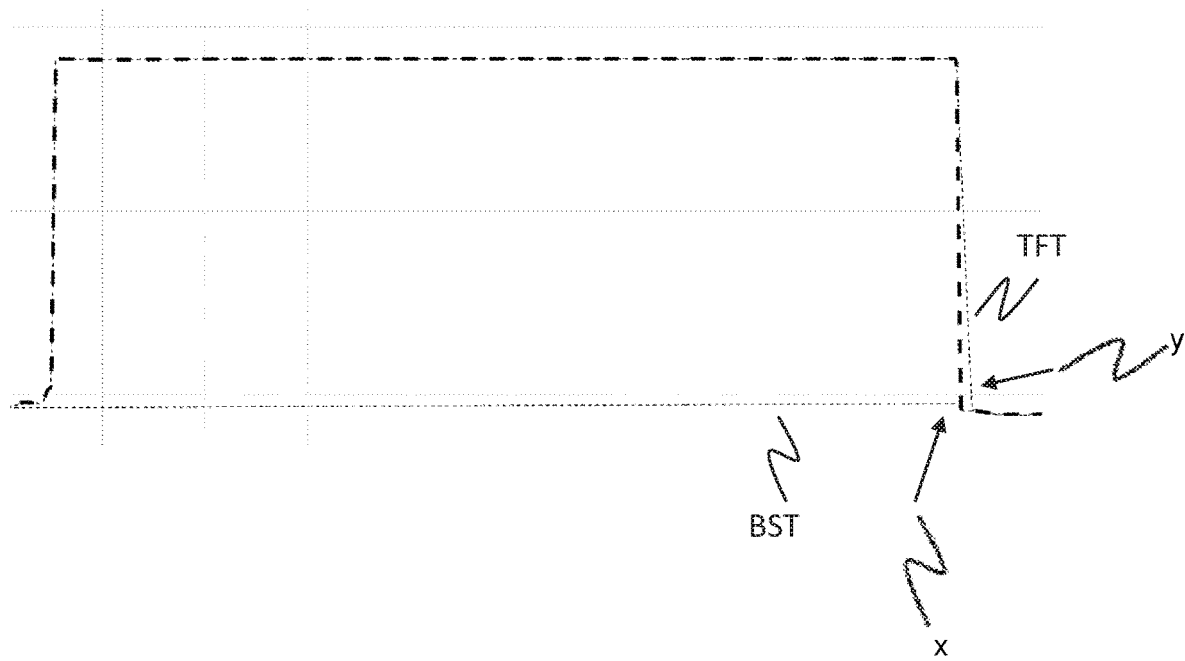
FIG. 8 shows a continuous signal together with the bottom slow tracker BST signal.

FIG. 8 depicts an exemplary continuous signal recorded during another injection (broken or dash-dot line), together with the bottom slow tracker BST signal and the top fast tracker TFT signal (both shown as dotted lines). The BST signal is gently relaxing towards the second value of the continuous signal (top plateau) such that there is a slight discrepancy between the BST signal and the continuous signal upon the latter returning to the first value (indicated by the bottom arrow x). At the same instant, the TFT signal is rapidly relaxing to the first value of the continuous signal, such as to appear to be closely following the latter (indicated by the right-hand side arrow y).

The time constant of the slow trackers is chosen to be fast enough to follow long term changes of the sensor and slow enough to provide a baseline. The time constant of the fast tracker signals is chosen to be fast enough to follow component-position motivated changes of the signal and slow enough to not follow potential short noise impulses, and may be smaller than the time constant of the slow tracker by a factor of at least 500 and preferably at least 5000. The thresholds are dependent on an absolute change in signal from the first to the second value, which in turn is dependent on geometric device design parameters, including distance traveled by the moving component, and tolerances of start position of the moving component, sensitivity of the sensors, and on the velocity of the trackers.

While the invention has been described in detail in the drawings and foregoing description, such description is to be considered illustrative or exemplary and not restrictive. Variations to the disclosed embodiments can be understood and effected by those skilled in the art and practicing the teachings herein, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims does not indicate that a combination of these elements or steps cannot be used to advantage, specifically, in addition to the actual claim dependency, any further meaningful claim combination shall be considered disclosed.

LIST OF DESIGNATIONS

1 Delivery device
10 Device housing
11 Syringe needle
12 Cover sleeve
13 Cover sleeve spring
13a, b Cover sleeve spring base
2 Electronic module
21 Position sensor
21a, b Induction coil
22 Position discriminator
23 Status evaluator
23a Evaluation table 24 Status indicators
25 Memory unit
26 Communication unit
31 Mobile device
32 Remote server

What is claimed is:

1. A method of evaluating a delivery status of a drug delivery device configured as an auto-injector with a container holding a liquid drug, comprising:
providing, by a position sensor, a continuous position sensor signal indicative of an instantaneous position of a base of a spring of the delivery device movable from a first position to a second position;
generating from the continuous position sensor signal, by a position discriminator, a binary position signal associated with the first position and the second position, wherein the binary position signal is indicative of whether the base of the spring is in the first position or the second position; and
deriving, by a status evaluator, the delivery status from the binary position signal, wherein the delivery status comprises a detected start or end of injection of the liquid drug or a detected lift-off of the drug delivery device from a patient.

2. The method of claim 1, further comprising:
(a) defining, by the position discriminator, for a continuous component position signal with a first value and a second value below the first value, a top slow tracker signal with predetermined relaxation properties; or
(b) defining, by the position discriminator, for a continuous component position signal with a first value and a second value above the first value, a bottom slow tracker signal with predetermined relaxation properties; and
using (a) or (b):
determining a difference between an instantaneous value of the continuous component position signal and either one of the top slow tracker signal or the bottom slow tracker signal, and
comparing the difference to a threshold to derive the binary position signal.

3. The method of claim 2, wherein a relaxation property of at least one slow tracker signal is determined by a linear drift parameter defining a linear variation of the slow tracker signal as long as an instantaneous value of the continuous component position signal does not exceed a top slow tracker signal value or fall below a bottom slow tracker signal value.

4. The method of claim 2, further comprising:
defining, by the position discriminator, for the continuous component position signal with the second value below the first value, a fast bottom tracker signal smaller than and approximating the continuous component position signal; and
determining the difference between the top slow tracker signal and the fast bottom tracker signal of the continuous component position signal; or
defining, by the position discriminator, for the continuous component position signal with the second value above the first value, a fast top tracker signal larger than and approximating the continuous component position signal; and
determining the difference between the fast top tracker signal and the bottom slow tracker signal of the continuous component position signal.

5. The method of claim 2, further comprising:
comparing the difference to a second threshold to derive a discrete position signal being associated with the first component position, the second component position, and a third component position.

6. The method of claim 1, wherein the step of deriving the delivery status is based on a table assigning each delivery status to a combination of binary augmented sensor signals, further comprising: deriving the delivery status based on a preceding delivery status.

7. A computer program which, when being executed by a processing unit of a monitoring unit of a drug delivery device configured as an auto-injector with a container holding a liquid drug, causes the processing unit to execute a method of evaluating a delivery status of the drug delivery device, comprising:
providing, by a position sensor, a continuous position sensor signal indicative of an instantaneous position of a cover sleeve or a cover sleeve spring base of the delivery device movable from a first position to a second position;
generating from the continuous position sensor signal, by a position discriminator, a binary position signal associated with the first position and the second position, wherein the binary position signal is indicative of whether the cover sleeve or the cover sleeve spring base is in the first position or the second position; and
deriving, by a status evaluator, the delivery status from the binary position signal, wherein the delivery status comprises a detected start or end of injection of the liquid drug or a detected lift-off of the drug delivery device from a patient.

8. The computer program of claim 7 wherein the method of evaluating a delivery status of the drug delivery device further comprises:
(a) defining, by the position discriminator, for a continuous component position signal with a first value and a second value below the first value, a top slow tracker signal with predetermined relaxation properties; or
(b) defining, by the position discriminator, for a continuous component position signal with a first value and a second value above the first value, a bottom slow tracker signal with predetermined relaxation properties; and
after (a) or (b):
determining a difference between an instantaneous value of the continuous component position signal and either one of the top slow tracker signal or the bottom slow tracker signal; and
comparing the difference to a threshold to derive the binary position signal.

9. The computer program of claim 8 wherein the method of evaluating a delivery status of the drug delivery device further comprises:
wherein a relaxation property of the slow tracker signal is determined by a linear drift parameter defining a linear variation of the slow tracker signal as long as an instantaneous value of the continuous component position signal does not exceed a top slow tracker signal value or fall below a bottom slow tracker signal value.

10. A monitoring unit for a drug delivery device configured as an auto-injector with a container holding a liquid drug, comprising:
a position discriminator for generating, from a continuous position sensor signal provided by a position sensor and indicative of an instantaneous position of a cover sleeve or a cover sleeve spring base of the delivery device movable from a first component position to a second component position, a binary position signal associated with the first component position and the second component position, wherein the binary position signal is indicative of whether the cover sleeve or the cover sleeve spring base is in the first component position or the second component position; and a status evaluator for deriving a delivery status from the binary position signal, wherein the delivery status comprises a detected start or end of injection of the liquid drug or a detected lift-off of the drug delivery device from a patient.

11. The monitoring unit of claim 10, wherein the monitoring unit comprises:
 a position discriminator for generating, from a further continuous position sensor signal provided by a further position sensor and indicative of an instantaneous position of a further component of the delivery device movable from a first further component position to a second further component position, a further binary position signal associated with the first further component position and the second further component position; and
 a status evaluator configured to derive the delivery status from both of the binary position signal and the further binary position signal.

12. The monitoring unit of claim 10, further comprising the position sensor adapted to provide the continuous position sensor signal indicative of the instantaneous position of the base of the spring.

13. The monitoring unit of claim 12, wherein the position sensor is adapted to provide a continuous position sensor signal indicative of a distance of the delivery device from a target injection site.

14. An electronic module for removable attachment to a drug delivery device configured as an auto-injector with a container holding a liquid drug, the module comprising a monitoring unit, comprising:
 a position discriminator for generating, from a continuous position sensor signal provided by a position sensor and indicative of an instantaneous position of a base of a spring of the drug delivery device movable from a first component position to a second component position, a binary position signal associated with the first component position and the second component position, wherein the binary position signal is indicative of whether the base of the spring is in the first component position or the second component position; and
 a status evaluator for deriving a delivery status from the binary position signal, wherein the delivery status comprises a detected start or end of injection of the liquid drug or a detected lift-off of the drug delivery device from a patient.

15. The electronic module of claim 14, further comprising a tag reader for reading information from a machine-readable tag mounted to a device housing of the drug delivery device, wherein the information comprises parameter values for the generation of the binary position signal by the position discriminator.

16. The electronic module of claim 14, wherein the monitoring unit further comprises:
 a position discriminator for generating, from a further continuous position sensor signal provided by a further position sensor and indicative of an instantaneous position of a further component of the delivery device movable from a first further component position to a second further component position, a further binary position signal associated with the first further component position and the second further component position; and
 a status evaluator configured to derive the delivery status from both of the binary position signal and the further binary position signal.

17. The electronic module of claim 14, wherein the monitoring unit comprises the position sensor adapted to provide the continuous position sensor signal indicative of the instantaneous position of the base of the spring.

18. The electronic module of claim 17, wherein the position sensor is adapted to provide a continuous position sensor signal indicative of a distance of the delivery device from a target injection site.

* * * * *